| United States Patent [19] | [11] | 4,170,703 |
|---|---|---|
| Johnson et al. | [45] | Oct. 9, 1979 |

[54] 5-HYDROXY-PGI₁ MORPHOLINYLAMIDES

[75] Inventors: Roy A. Johnson; John C. Sih, both of Kalamazoo, Mich.

[73] Assignee: The Upjohn Company, Kalamazoo, Mich.

[21] Appl. No.: 899,200

[22] Filed: Apr. 24, 1978

Related U.S. Application Data

[63] Continuation-in-part of Ser. No. 815,648, Jul. 14, 1977, Pat. No. 4,110,532.

[51] Int. Cl.² ............................................. C07D 407/02
[52] U.S. Cl. ................................... 542/426; 542/430; 544/151
[58] Field of Search ................. 544/151; 542/430, 426

[56] References Cited

U.S. PATENT DOCUMENTS

| 3,846,475 | 11/1974 | Crabbe et al. .......................... 542/429 |
| 4,028,419 | 6/1974 | Nelson ................................ 260/345.2 |

OTHER PUBLICATIONS

Johnson et al., Prostaglandins.

*Primary Examiner*—Arthur P. Demers
*Attorney, Agent, or Firm*—Robert A. Armitage

[57] ABSTRACT

The present invention provides 5-hydroxy-PGI₁, morpholinylamides, which are useful pharmacological agents. These analogs of prostaglandin I₁ are useful for the stimulation of mammalian smooth muscle tissues.

47 Claims, No Drawings

5-HYDROXY-PGI$_1$ MORPHOLINYLAMIDES

CROSS REFERENCE TO RELATED APPLICATIONS

This application is a continuation-in-part of Ser. No. 815,648, filed July 14, 1977, issued as U.S. Pat. No. 4,110,532 on Aug. 29, 1978.

The present invention relates to 5-hydroxy-PGI$_1$, morpholinylamides, the essential material constituting a disclosure thereof being hereby incorporated by reference from U.S. Pat. No. 4,110,532, issued Aug. 29, 1978. In particular the present invention relates to morpholinylamides of 5-hydroxy-PGI$_1$ corresponding to the various carboxylic acids disclosed and claimed in U.S. Pat. No. 4,110,532.

We claim:

1. A prostacyclin analog of the formula

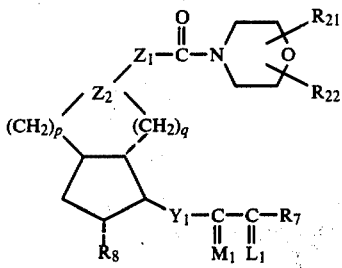

wherein $Z_2$ is

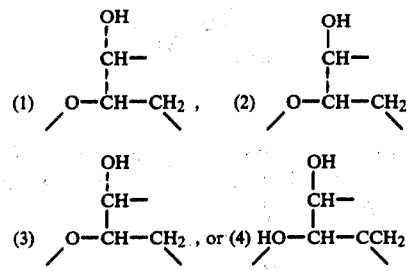

wherein one of p or q is the integer zero or one and the other is the integer zero;
wherein $Z_1$ is
(1) —(CH$_2$)$_g$—CH$_2$—CH$_2$—,
(2) —(CH$_2$)$_g$—CH$_2$—CF$_2$—, or
(3) trans—(CH$_2$)$_g$—CH=CH—,
wherein g is the integer one, 2, or 3 when q is zero and zero, one, or 2 when q is one;
wherein $R_8$ is hydrogen, hydroxy, or hydroxymethyl;
wherein $Y_1$ is
(1) trans—CH=CH—,
(2) cis—CH=CH—,
(3) —CH$_2$CH$_2$—,
(4) trans—CH=C(Hal)—, or
(5) —C≡C—
wherein Hal is chloro or bromo;
wherein $M_1$ is

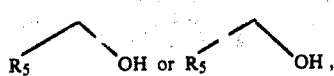

wherein $R_5$ is hydrogen or alkyl with one to 4 carbon atoms, inclusive:
wherein $L_1$ is

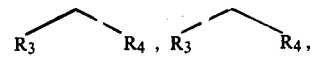

or a mixture of

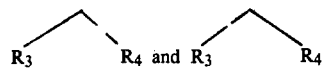

wherein $R_3$ and $R_4$ are hydrogen, methyl, or fluoro, being the same or different, with the proviso that one of $R_3$ and $R_4$ is fluoro only when the other is hydrogen or fluoro;
wherein $R_{21}$ and $R_{22}$ are hydrogen, alkyl of one to 12 carbon atoms, inclusive; aralkyl of 7 to 12 carbon atoms, inclusive, phenyl, phenyl substituted with one, 2, or 3 chloro or alkyl of one to 3 carbon atoms, inclusive, or phenyl substituted with hydroxycarbonyl or alkoxycarbonyl of one to 4 carbon atoms, inclusive; and
wherein $R_7$ is
(1) —(CH$_2$)$_3$—CH$_3$,

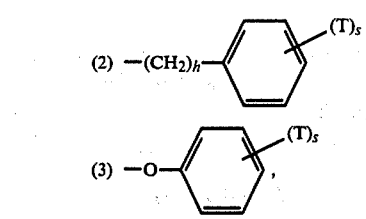

wherein h is the integer zero or one; s is the integer zero, one, 2, or 3; and T is chloro, fluoro, trifluoromethyl, alkyl of one to 3 carbon atoms, inclusive, or with the proviso that not more than two T's are other than alkyl.

2. A prostacyclin analog according to claim 1, wherein $R_8$ is hydroxymethyl.

3. (5S)-11-Deoxy-11α-hydroxymethyl-5-hydroxy-6α-PGI$_1$, morpholinylamide, a prostacyclin analog according to claim 2.

4. A prostacyclin analog according to claim 1, wherein $R_8$ is hydrogen.

5. (5S)-11-Deoxy-5-hydroxy-6α-PGI$_1$, morpholinylamide, a prostacyclin analog according to claim 4.

6. A prostacyclin analog according to claim 1, wherein $R_8$ is hydroxy.

7. A prostacyclin analog according to claim 6, wherein q is one.

8. 7α-Homo-2-nor-(5S)-5-hydroxy-6α-PGI$_1$, morpholinylamide, a prostacyclin analog according to claim 7.

9. A prostacyclin analog according to claim 6, wherein p is one.

10. 9-Hydroxymethyl-(5S)-5-hydroxy-6α-PGI$_1$, morpholinylamide, a prostacyclin analog according to claim 9.

11. A prostacyclin analog according to claim 6, wherein $Z_2$ is

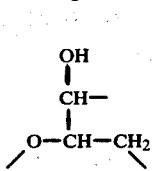

12. A prostacyclin analog according to claim 6, wherein $Z_2$ is

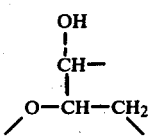

13. (5R)-5-Hydroxy-6β-PGI$_1$, morpholinylamide, a prostacyclin analog according to claim 12.

14. A prostacyclin analog according to claim 6, wherein $Z_2$ is

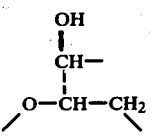

15. (5S)-5-Hydroxy-6α-PGI$_1$, morpholinylamide, a prostacyclin analog according to claim 14.

16. (5S)-5-Hydroxy-15-methyl-6α-PGI$_1$, morpholinylamide, a prostacyclin analog according to claim 14.

17. (5S)-5-Hydroxy-16,16-dimethyl-6α-PGI$_1$, morpholinylamide, a prostacyclin analog according to claim 14.

18. A prostacyclin analog according to claim 11, wherein $Z_2$ is

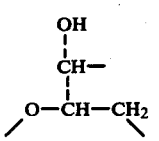

19. A prostacyclin analog according to claim 18, wherein $Y_1$ is cis—CH=CH—.

20. (5R)-5-Hydroxy-cis-13-6α-PGI$_1$, morpholinylamide, a prostacyclin analog according to claim 19.

21. A prostacyclin analog according to claim 18, wherein $Y_1$ is —C≡C—.

22. (5R)-5-Hydroxy-13,14-didehydro-6α-PGI$_1$, morpholinylamide, a prostacyclin analog according to claim 21.

23. A prostacyclin analog according to claim 18, wherein $Y_1$ is trans—CH=C(Hal)—.

24. (5R)-5-Hydroxy-14-chloro-6α-PGI$_1$, morpholinylamide, a prostacyclin analog according to claim 23.

25. A prostacyclin analog according to claim 18, wherein $Y_1$ is —CH$_2$CH$_2$—.

26. (5R)-5-Hydroxy-13,14-dihydro-6α-PGI$_1$, morpholinylamide, a prostacyclin analog according to claim 25.

27. A prostacyclin analog according to claim 18, wherein $Y_1$ is trans—CH=CH—.

28. A prostacyclin analog according to claim 27, wherein $Z_1$ is —(CH$_2$)$_g$—CH$_2$—CF$_2$—.

29. 2,2-Difluoro-(5R)-5-hydroxy-6α-PGI$_1$, morpholinylamide, a prostacyclin analog according to claim 28.

30. A prostacyclin analog according to claim 27, wherein $Z_1$ is trans—(CH$_2$)$_g$—CH=CH—.

31. trans-2,3-Didehydro-(5R)-5-hydroxy-6α-PGI$_1$, morpholinylamide, a prostacyclin analog according to claim 30.

32. A prostacyclin analog according to claim 27, wherein $Z_1$ is —(CH$_2$)$_g$—CH$_2$—CH$_2$—.

33. A prostacyclin analog according to claim 32, wherein g is one.

34. A prostacyclin analog according to claim 33, wherein $R_7$ is

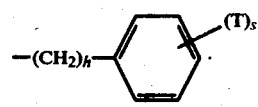

35. (5R)-5-Hydroxy-17-phenyl-18,19,20-trinor-6α-PGI$_1$, morpholinylamide, a prostacyclin analog according to claim 34.

36. A prostacyclin analog according to claim 33, wherein $R_7$ is

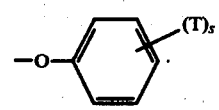

37. (5R)-5-Hydroxy-16-phenoxy-17,18,19,20-tetranor-6α-PGI$_1$, morpholinylamide, a prostacyclin analog according to claim 36.

38. A prostacyclin analog according to claim 33, wherein $R_7$ is —(CH$_2$)$_3$—CH$_3$.

39. A prostacyclin analog according to claim 38, wherein $R_5$ is methyl.

40. (5R)-5-Hydroxy-15-methyl-6α-PGI$_1$, morpholinylamide, a prostacyclin analog according to claim 39.

41. A prostacyclin analog according to claim 38, wherein $R_5$ is hydrogen.

42. A prostacyclin analog according to claim 41, wherein at least one of $R_3$ and $R_4$ is fluoro.

43. (5R)-5-Hydroxy-16,16-difluoro-6α-PGI$_1$, morpholinylamide, a prostacyclin analog according to claim 42.

44. A prostacyclin analog according to claim 41, wherein at least one of $R_3$ and $R_4$ is methyl.

45. (5R)-5-Hydroxy-16,16-dimethyl-6α-PGI$_1$, morpholinylamide, a prostacyclin analog according to claim 44.

46. A prostacyclin analog according to claim 41, wherein $R_3$ and $R_4$ are both hydrogen.

47. (5R)-5-Hydroxy-6α-PGI$_1$, morpholinylamide, a prostacyclin analog according to claim 46.

* * * * *

UNITED STATES PATENT OFFICE
CERTIFICATE OF CORRECTION

Patent No. 4,170,703  Dated 9 October 1979

Inventor(s) Roy A. Johnson and John C. Sih

It is certified that error appears in the above-identified patent and that said Letters Patent are hereby corrected as shown below:

Column 3, line 40, "according to claim 11" should read
-- according to claim 6 --.

Signed and Sealed this

Twenty-ninth Day of July 1980

[SEAL]

*Attest:*

SIDNEY A. DIAMOND

*Attesting Officer*  *Commissioner of Patents and Trademarks*